US012178573B2

(12) United States Patent
Ota et al.

(10) Patent No.: US 12,178,573 B2
(45) Date of Patent: Dec. 31, 2024

(54) BILIRUBIN CONCENTRATION MEASUREMENT SYSTEM

(71) Applicants: National University Corporation YOKOHAMA National University, Yokohama (JP); Public University Corporation Yokohama City University, Yokohama (JP)

(72) Inventors: Hiroki Ota, Yokohama (JP); Yutaka Isoda, Yokohama (JP); Go Inamori, Yokohama (JP); Shuichi Ito, Kanagawa (JP); Azusa Uozumi, Kanagawa (JP)

(73) Assignees: NATIONAL UNIVERSITY CORPORATION YOKOHAMA NATIONAL UNIVERSITY, Yokohama (JP); PUBLIC UNIVERSITY CORPORATION YOKOHAMA CITY UNIVERSITY, Yokohama (JP)

( * ) Notice: Subject to any disclaimer, the term of this patent is extended or adjusted under 35 U.S.C. 154(b) by 843 days.

(21) Appl. No.: 17/414,935

(22) PCT Filed: Dec. 17, 2019

(86) PCT No.: PCT/JP2019/049449
§ 371 (c)(1),
(2) Date: Jun. 16, 2021

(87) PCT Pub. No.: WO2020/129989
PCT Pub. Date: Jun. 25, 2020

(65) Prior Publication Data
US 2022/0047192 A1    Feb. 17, 2022

(30) Foreign Application Priority Data
Dec. 21, 2018    (JP) .................. 2018-239555

(51) Int. Cl.
*A61B 5/145*    (2006.01)
*A61B 5/00*    (2006.01)
*A61B 5/1455*    (2006.01)

(52) U.S. Cl.
CPC ........ *A61B 5/14546* (2013.01); *A61B 5/0002* (2013.01); *A61B 5/1455* (2013.01); *A61B 5/4255* (2013.01); *A61B 2503/045* (2013.01)

(58) Field of Classification Search
None
See application file for complete search history.

(56) References Cited

U.S. PATENT DOCUMENTS 5,086,229 A  *  2/1992  Rosenthal ............ G01N 21/359
                                                  250/339.04
5,913,819 A  *  6/1999  Taylor .................. A61B 5/6833
                                                  600/323

(Continued)

FOREIGN PATENT DOCUMENTS

EP    0747002 A1    12/1996
JP    H08332182 A   12/1996

(Continued)

OTHER PUBLICATIONS

Teh, H. et al., "Sensor data quality: a systematic review," Journal of Big Data, vol. 7, No. 11, Feb. 20, 2020, 50 pages.

(Continued)

*Primary Examiner* — Benjamin S Melhus
*Assistant Examiner* — Samuel C Kim
(74) *Attorney, Agent, or Firm* — McCoy Russell LLP

(57) ABSTRACT

A bilirubin concentration measurement system including: a sensor device attachable to a subject; and a terminal device capable of wirelessly communicating with the sensor device. The sensor device includes: a light emitting diode that emits blue light; a light emitting diode that emits green light; a (Continued)

OUTPUT OF LIGHT DETECTION ELEMENT (BLUE LIGHT)

light detection diode that detects reflected light that is the blue light having been incident on skin of the subject and reflected, and detects reflected light that is the green light having been incident on the skin of the subject and reflected; and a communication unit that wirelessly transmits information about intensities of the reflected light detected by the photodiode. The terminal device includes: a communication unit that receives the information about the intensities of the reflected light transmitted from the sensor device; and a computing unit that calculates a bilirubin concentration using the information about the intensities of the reflected light.

8 Claims, 11 Drawing Sheets

(56) References Cited

U.S. PATENT DOCUMENTS

| | | | |
|---|---|---|---|
| 6,402,691 B1* | 6/2002 | Peddicord | G16Z 99/00 |
| | | | 455/39 |
| 6,847,835 B1* | 1/2005 | Yamanishi | A61B 5/443 |
| | | | 600/315 |
| 2002/0111541 A1* | 8/2002 | Bibl | G08B 25/016 |
| | | | 128/903 |
| 2004/0138540 A1* | 7/2004 | Baker, Jr. | A61B 5/145 |
| | | | 600/336 |
| 2008/0039778 A1* | 2/2008 | Goldie | A61J 11/0005 |
| | | | 215/11.1 |
| 2008/0275307 A1* | 11/2008 | Poschmann | G08B 21/028 |
| | | | 600/300 |
| 2012/0165618 A1* | 6/2012 | Algoo | A61B 5/744 |
| | | | 600/300 |
| 2013/0053654 A1* | 2/2013 | Caduff | A61B 5/441 |
| | | | 600/323 |
| 2014/0243681 A1* | 8/2014 | Hielscher | A61B 5/0075 |
| | | | 600/476 |
| 2015/0148623 A1 | 5/2015 | Benaron | |
| 2017/0071513 A1* | 3/2017 | Hoss | A61B 5/14546 |
| 2018/0228433 A1* | 8/2018 | Kim | A61B 5/14532 |
| 2019/0008432 A1* | 1/2019 | Bashan | A61B 5/684 |
| 2021/0038144 A1* | 2/2021 | Watanabe | A61B 5/0004 |

FOREIGN PATENT DOCUMENTS

| | | |
|---|---|---|
| JP | 2000279398 A | 10/2000 |
| JP | 2011163953 A | 8/2011 |
| JP | 2015514512 A | 5/2015 |
| JP | 2016096977 A | 5/2016 |
| JP | 2017504446 A | 2/2017 |
| WO | 2013158815 A2 | 10/2013 |
| WO | 2015084947 A1 | 6/2015 |
| WO | 2017115361 A1 | 7/2017 |

OTHER PUBLICATIONS

European Patent Office, Extended European Search Report Issued in Application No. 19898117.7, Aug. 10, 2022, Germany, 9 pages.

ISA Japan Patent Office, International Search Report Issued in Application No. PCT/JP2019/049449, Mar. 24, 2020, WIPO, 4 pages.

Japanese Patent Office, Office Action Issued in Application No. 2020-561462, Aug. 15, 2023, 9 pages.

* cited by examiner

BILIRUBIN CONCENTRATION MEASUREMENT SYSTEM

CROSS REFERENCE TO RELATED APPLICATIONS

The present application is a U.S. National Phase of International Application No. PCT/JP2019/049449 entitled "BILIRUBIN CONCENTRATION MEASUREMENT SYSTEM," and filed on Dec. 17, 2019. International Application No. PCT/JP2019/049449 claims priority to Japanese Patent Application No. 2018-239555 filed on Dec. 21, 2018. The entire contents of each of the above-listed applications are hereby incorporated by reference for all purposes.

TECHNICAL FIELD

The present invention relates to a bilirubin concentration measurement system and, in particular, to a bilirubin concentration measurement system that includes a sensor device attachable to a subject.

BACKGROUND AND SUMMARY

Newborns, babies and infants have immaturely developed bodies, and their vital signs are necessarily checked. In particular, newborns and babies have immature livers. Accordingly, the functions of the livers are required to be periodically monitored. One of important parameters indicating hepatic functions is bilirubin, which is generated during degradation of hemoglobin. Since the newborns and babies have immature livers, they cannot quickly degrade generated bilirubin. As a result, undegraded bilirubin is accumulated in skin tissue to cause jaundice. If appropriate treatment is not applied when jaundice is caused, bilirubin can be deposited in the brain and possibly cause a brain damage. The bilirubin allowance level depends on the ages (ages in month) of newborns and babies. Accordingly, in order to find the symptoms of jaundice as early as possible, it is important to measure the bilirubin concentrations (bilirubin values) of newborns and infants continuously.

The bilirubin concentration is measured using a method of sampling and directly measuring blood (blood sampling method), or an optical method. The blood sampling method has an advantage that can highly accurately measure bilirubin values. However, the method is invasive, and requires time and effort for measurement accordingly. On the other hand, the optical method is non-invasive. Consequently, the method can more easily achieve measurement than the invasive blood sampling method. For such a reason, the optical method is widely used to measure the bilirubin concentration (Patent Literatures 1 and 2).

CITATION LIST

Patent Literature

Japanese Unexamined Patent Application Publication No. 2000-279398
Japanese Unexamined Patent Application Publication No. 2011-163953

Technical Problem

As described above, the optical method is non-invasive. Consequently, this method can more easily measure the bilirubin concentration than the invasive blood sampling method. However, conventional bilirubin concentration measurement apparatuses that use the optical method are large in size. Accordingly, they impose heavy burden on medical staff and subjects (newborns and babies). Consequently, it is difficult to measure the bilirubin concentration continuously.

Furthermore, use of the conventional bilirubin concentration measurement apparatus requires medical staff to conduct measurement for a subject, with the bilirubin concentration measurement apparatus being in contact with the subject, at every time of measurement. Accordingly, it is difficult to monitor the bilirubin concentration continuously. In particular, the bilirubin concentrations of newborns and babies sometimes change rapidly. In the case of using the conventional bilirubin concentration measurement apparatus, it is difficult to detect such rapid change in bilirubin concentration.

In view of the above problems, the present invention has an object to provide a bilirubin concentration measurement system that is small in size and capable of continuously monitoring the bilirubin concentration.

Solution to Problem

A bilirubin concentration measurement system according to an aspect of the present invention includes: a sensor device attachable to a subject; and a terminal device capable of wirelessly communicating with the sensor device. The sensor device includes: a first light emitting element that emits light in a first wavelength band at a first timing; a second light emitting element that emits light in a second wavelength band at a second timing; a light detection element that detects first reflected light that is the light in the first wavelength band having been incident on skin of the subject and been reflected at the first timing, and detects second reflected light that is the light in the second wavelength band having been incident on the skin of the subject and been reflected at the second timing; and a first communication unit that wirelessly transmits information about intensities of the first and second reflected light detected by the light detection element. The terminal device includes: a second communication unit that receives the information about the intensities of the first and second reflected light transmitted from the first communication unit; and a computing unit that calculates a bilirubin concentration using the information about the intensities of the first and second reflected light.

Advantageous Effects of Invention

The present invention can provide the bilirubin concentration measurement system that is small in size and capable of continuously monitoring the bilirubin concentration.

DETAILED DESCRIPTION

Figure 1:
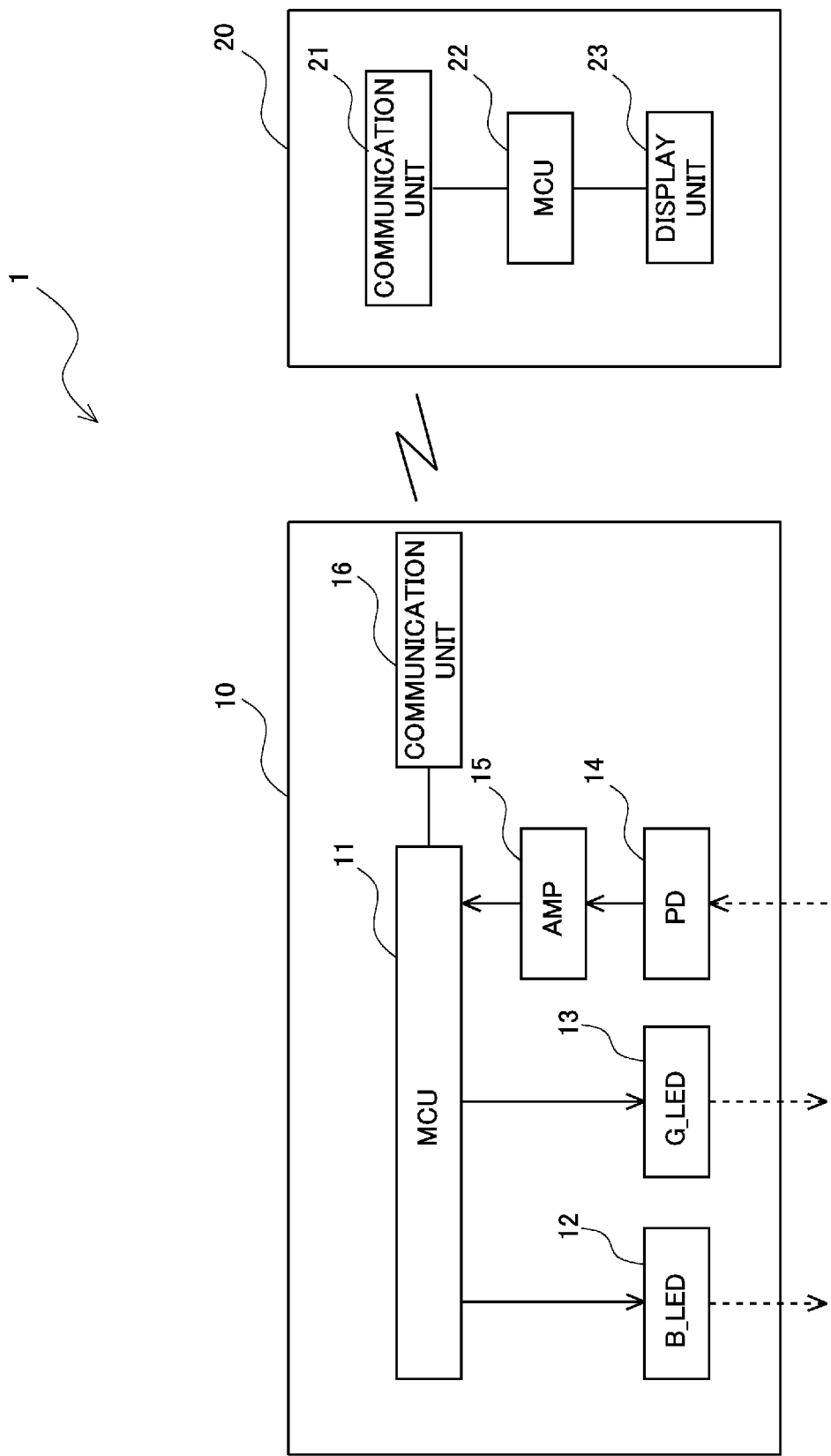
FIG. 1 is a block diagram for illustrating a bilirubin concentration measurement system according to an embodiment.

Hereinafter, referring to the drawings, embodiments of the present invention are described.

FIG. 1 is a block diagram for illustrating a bilirubin concentration measurement system according to an embodiment. As shown in FIG. 1, the bilirubin concentration measurement system 1 according to this embodiment includes a sensor device 10, and a terminal device 20. The sensor device 10 is configured to be attachable to a subject (a newborn or a baby). The terminal device 20 is configured to be capable of wirelessly communicating with the sensor device 10.

The sensor device 10 includes a control circuit 11, light emitting elements 12 and 13, and a light detection element 14, an amplifier 15, and a communication unit 16. The terminal device 20 includes a communication unit 21, a computing unit 22, and a display unit 23.

The control circuit 11 included in the sensor device 10 controls each of circuit elements included in the sensor device 10. The control circuit 11 can be configured using an MCU (Micro Controller Unit), for example.

The light emitting element 12 emits light in a blue wavelength band (e.g., 470 nm) (hereinafter, also described as blue light) at a predetermined timing. The light emitting element 12 can be configured using a blue light emitting diode (LED), for example. The light emitting element 12 is configured to emit light according to a control signal (drive signal) supplied from the control circuit 11. In other words, the light emitting timing of the light emitting element 12 is controlled using the control circuit 11.

The light emitting element 13 emits light in a green wavelength band (e.g., 570 nm) (hereinafter, also described as green light) at a predetermined timing. The light emitting element 13 can be configured using a green light emitting diode (LED), for example. The light emitting element 13 is configured to emit light according to a control signal (drive signal) supplied from the control circuit 11. In other words, the light emitting timing of the light emitting element 13 is controlled using the control circuit 11.

The light detection element 14 detects reflected light that is blue light of the light emitting element 12 having entered skin of a subject and been reflected. Likewise, the light detection element 14 detects reflected light that is green light of the light emitting element 13 having entered the skin of the subject and been reflected. The light detection element 14 can be configured using an element capable of outputting an electric signal (voltage signal) according to the intensity of the reflected light. The light detection element 14 can be configured using a photodiode, for example.

The amplifier 15 amplifies the electric signal supplied from the light detection element 14, and supplies the amplified signal to the control circuit 11. Note that in a case where the control circuit 11 can directly deal with the electric signal (voltage signal) generated by the light detection element 14, the amplifier 15 may be omitted.

The control circuit 11 supplies the communication unit 16 with the electric signal supplied from the amplifier 15. Here, the electric signal supplied from the amplifier 15 corresponds to information about the intensities of the reflected light detected by the light detection element 14. For example, the control circuit 11 may convert the electric signal supplied from the amplifier 15, which is an analog signal, into a digital signal, and supply the converted digital signal to the communication unit 16.

The communication unit 16 wirelessly transmits the electric signal supplied from the control circuit 11 (i.e., the information about the intensities of the reflected light), to the terminal device 20. In other words, the communication unit 16 wirelessly transmits, to the terminal device 20, the information about the intensities of the reflected light detected by the light detection element 14.

The communication unit 21 of the terminal device 20 receives the information about the intensities of the reflected light, the information having been transmitted from the communication unit 16 of the sensor device 10. The information about the intensities of the reflected light received by the communication unit 21 is supplied to the computing unit 22.

For example, the communication unit 16 of the sensor device 10 and the communication unit 21 of the terminal device 20 can wirelessly communicate with each other using a wireless LAN, Bluetooth®, or a mobile phone network, such as of 3G, 4G or 5G. The network to be used can be appropriately selected in conformity with the distance and the like between the communication unit 16 and the communication unit 21.

The computing unit 22 calculates the bilirubin concentration using the information about the intensities of the reflected light received by the communication unit 21. In other words, the computing unit 22 calculates the bilirubin concentration, using the intensity of the reflected light that is the blue light of the light emitting element 12 having entered the skin of the subject and been reflected, and the intensity of the reflected light that is the green light of the light emitting element 13 having entered the skin of the subject and been reflected. Note that a specific method of calculating the bilirubin concentration is described later. The computing unit 22 can be configured using an MCU (Micro Controller Unit), for example.

The display unit 23 displays the bilirubin concentration calculated by the computing unit 22. The display unit 23 can be configured using a liquid crystal display, for example. For example, when the calculated bilirubin concentration exceeds a predetermined reference value, a warning message may be displayed on the display unit 23.

The terminal device 20 can be configured using a smartphone, a tablet terminal or the like, for example. For example, when the calculated bilirubin concentration exceeds the predetermined reference value, a warning sound may be issued from a speaker included in the terminal device 20.

The settings (e.g., settings of the light emitting timings and light intensities of the light emitting elements 12 and 13, etc.) of the sensor device 10 may be configured using the terminal device 20. In this case, setting information on the sensor device 10 is generated by the computing unit 22 of the terminal device 20. The generated setting information is transmitted from the communication unit 21 of the terminal device 20 to the communication unit 16 of the sensor device 10. The communication unit 16 of the sensor device 10 supplies the control circuit 11 with the setting information received from the terminal device 20. Accordingly, the control circuit 11 can change the settings (e.g., settings of the light emitting timings and light intensities of the light emitting elements 12 and 13, etc.) of the sensor device 10.

Figure 2:
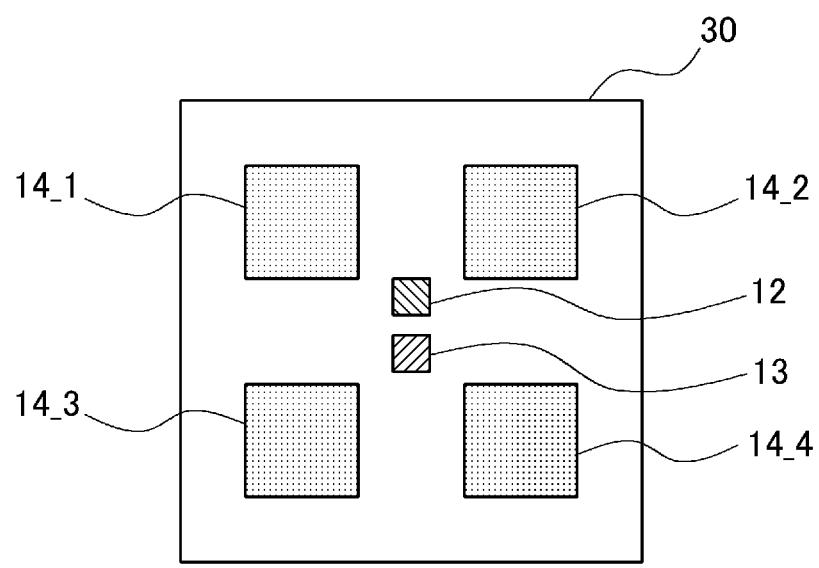
FIG. 2 is a diagram for illustrating an arrangement example of light emitting elements and light detection elements included in a sensor device according to the embodiment.

FIG. 2 is a diagram for illustrating an arrangement example of the light emitting elements 12 and 13 and light detection elements 14 included in a sensor device 10 according to the embodiment. In the arrangement example shown in FIG. 2, the two light emitting elements 12 and 13 and the four light detection elements 14_1 to 14_4 are implemented on an identical substrate 30. The four light detection elements 14_1 to 14_4 are arranged around the two light emitting elements 12 and 13. The light emitting surfaces of the two light emitting elements 12 and 13 and the light receiving surfaces of the four light detection elements 14_1 to 14_4 are configured to be on the same plane.

In the configuration example shown in FIG. 2, the light detection elements 14_1 to 14_4 are arranged so as to encircle the light emitting elements 12 and 13. Accordingly, it is possible to effectively detect reflected light which is light that is originated from the light emitting elements 12 and 13, then incident on skin of the subject and reflected. Consequently, the sensor device 10 can be reduced in size. Note that the arrangement example shown in FIG. 2 is only an example. For the bilirubin concentration measurement system according to this embodiment, the arrangements and the numbers of light emitting elements 12 and 13 and light detection elements 14 can be freely determined.

Figure 3:
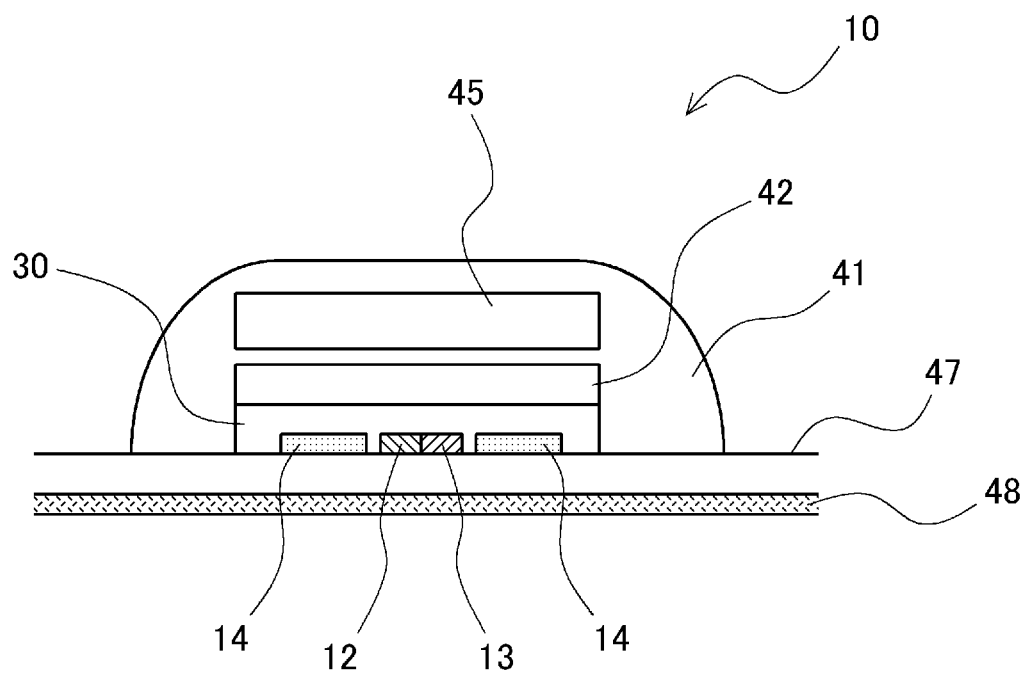
FIG. 3 is a sectional view for illustrating a configuration example of the sensor device according to the embodiment.

FIG. 3 is a sectional view for illustrating a configuration example of the sensor device according to this embodiment. As shown in FIG. 3, the sensor device 10 includes the substrate 30, an exterior resin 41, a substrate 42, and a battery 45. The sensor device 10 is attached to the surface of skin of a subject 47.

The substrate 30 is a substrate on which the light emitting elements 12 and 13 and the light detection elements 14 are implemented. The substrate 42 is a substrate on which circuit elements, such as the control circuit 11, the amplifier 15 and the communication unit 16 (see FIG. 1), are implemented. The substrate 30 and the substrate 42 are stacked in the vertical direction. The battery 45 is a battery for driving the sensor device 10, and can be configured using a lithium-ion secondary battery or the like.

As shown in FIG. 3, the substrate 30, the substrate 42 and the battery 45 are implemented in the exterior resin 41. Specifically, the exterior resin 41 allows the substrate 30, the substrate 42 and the battery 45 to be implemented, so as to enclose these elements. The light emitting surfaces of the light emitting elements 12 and 13, and the light receiving surfaces of the light detection elements 14 are exposed from a surface of the exterior resin 41 facing the subject 47. Consequently, when the sensor device 10 is attached to the surface of the skin of the subject 47, this device is attached such that the light emitting surfaces of the light emitting elements 12 and 13 and the light receiving surfaces of the light detection elements 14 can be in contact with the subject 47.

Preferably, the surface of the exterior resin 41 facing the subject 47 has a shape corresponding to the position of the subject 47 to which the sensor device 10 is attached. For example, in order to attach the sensor device 10, which is a wearable device, onto a forehead of a newborn, the sensor device 10 is configured to have an attachment surface having a shape corresponding to the forehead of the newborn (a shape having a predetermined curve). For example, the substrates 30 and 42 may be flexible polyimide substrates. Such a configuration can bring the sensor device 10 into close contact with the skin surface of the subject 47. For example, the exterior resin 41 can be configured using silicone rubber, PDMS (polydimethylsiloxane), epoxy resin, polyurethane or the like.

As shown in FIG. 3, when the light emitting element 12 emits light in a state where the sensor device 10 is attached on the surface of the skin of the subject 47, blue light from the light emitting element 12 is incident on the skin of the subject 47. A part of the blue light incident on the skin reaches a blood vessel 48 of the subject 47 and is reflected, and is detected as reflected light by the light detection elements 14. Likewise, when the light emitting element 13 emits light in the state where the sensor device 10 is attached on the surface of the skin of the subject 47, green light from the light emitting element 13 is incident on the skin of the subject 47. A part of the green light incident on the skin reaches the blood vessel 48 of the subject 47 and is reflected, and is detected as reflected light by the light detection elements 14. Note that "reflected light" includes light from the light emitting elements 12 and 13 having been absorbed by or passed through the skin surface.

Next, a method of measuring the bilirubin concentration using the bilirubin concentration measurement system according to this embodiment is described. First a bilirubin concentration measurement principle is described. The bilirubin concentration measurement system according to this embodiment measures the bilirubin concentration in the blood of a subject using an optical method. Specifically, the bilirubin concentration is measured using the difference between the absorbance (absorptance) of bilirubin in the blue wavelength band, and the absorbance (absorptance) of bilirubin in the green wavelength band.

Figure 4:
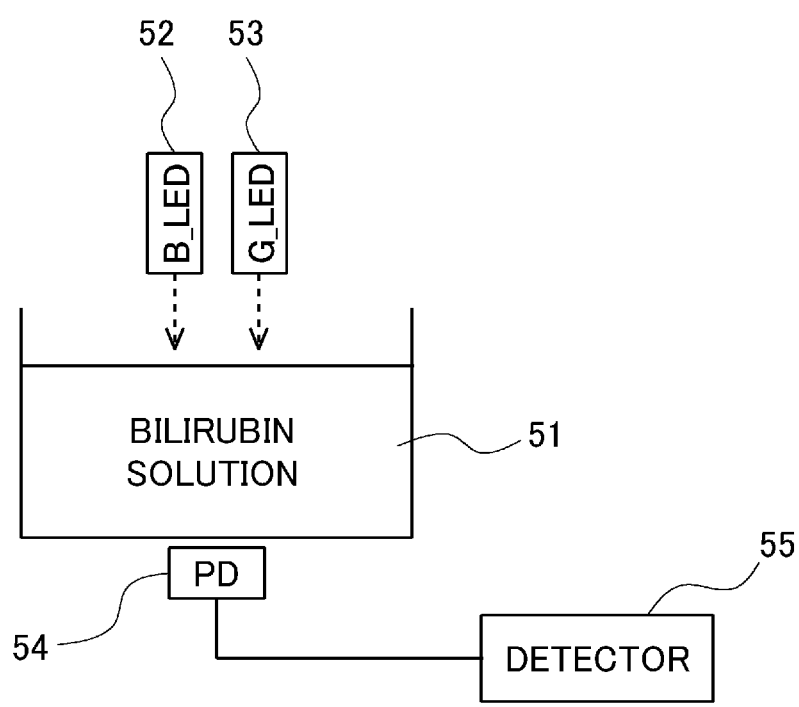
FIG. 4 is a diagram for illustrating a bilirubin concentration measurement principle.

FIG. 4 is a diagram for illustrating the bilirubin concentration measurement principle. In a measurement apparatus shown in FIG. 4, a blue light emitting element 52 and a green light emitting element 53 are arranged above a container that contains a bilirubin solution 51. Furthermore, a light detection element 54 is arranged below the container, which contains the bilirubin solution 51. The intensity of light detected by the light detection element 54 is converted into predetermined data by a detector 55. Through use of the apparatus shown in FIG. 4, the absorbance (absorptance) of blue light having passed through the bilirubin solution 51, and the absorbance (absorptance) of green light having passed through the bilirubin solution 51 can be measured.

Figure 5:
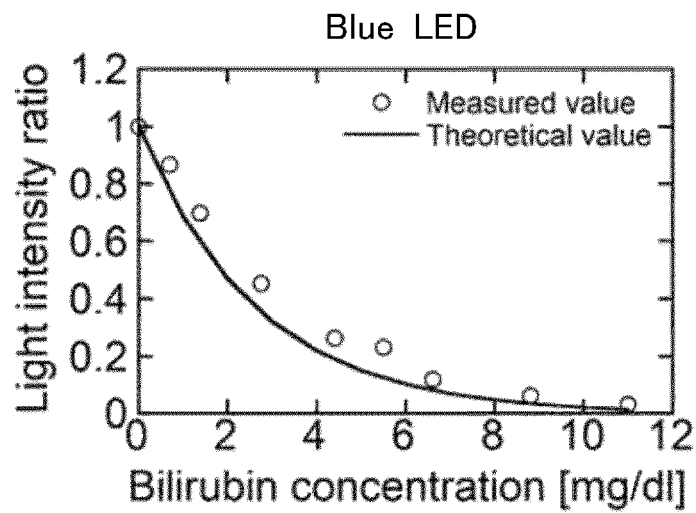
FIG. 5 is a graph showing the relationship between the bilirubin concentration and light intensity (in a case of blue light).
Figure 6:
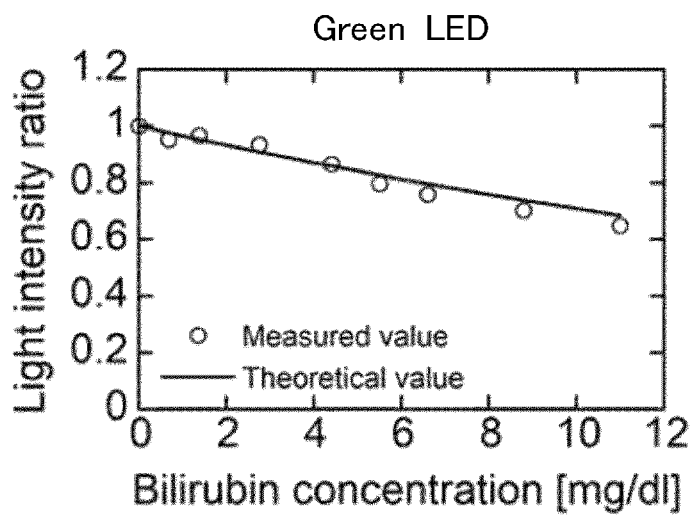
FIG. 6 is a graph showing the relationship between the bilirubin concentration and light intensity (in a case of green light).

FIG. 5 is a graph showing the relationship between the bilirubin concentration and light intensity (in the case of blue light). FIG. 6 is a graph showing the relationship between the bilirubin concentration and light intensity (in the case of green light). In the graphs shown in FIGS. 5 and 6, the light intensity is normalized to be one when the bilirubin concentration is zero. As shown in FIGS. 5 and 6, for both the cases of blue light and green light, the intensity of light detected by the light detection element 54 decreases with increase in bilirubin concentration. In particular, in the case of blue light, the attenuation of light intensity is higher than that in the case of green light. Consequently, the blue light and the green light have different absorptances in the bilirubin solution. In particular, with respect to the blue light, the absorptance of light in the bilirubin solution is large. Note that as shown in FIGS. 5 and 6, the measured values approximately coincide with respective theoretical values.

In this embodiment, the bilirubin concentration is measured using the difference between the absorptance of blue light and the absorptance of green light for bilirubin. A specific method is described below.

In the bilirubin concentration measurement system according to this embodiment, the computing unit 22 of the terminal device 20 calculates the bilirubin concentration, using information about the intensity of the reflected light of blue light and the intensity of the reflected light of green light, and the following Expression 1. The following Expression 1 is an equation for obtaining the bilirubin concentration, the equation is derived using the Lambert-Beer law.

[Math. 1]
$$C = D\left[-\log_{10}\frac{I(\lambda_1)}{I_0(\lambda_1)} + 1.95\log_{10}\frac{I(\lambda_2)}{I_0(\lambda_2)} + R\right]$$ Expression 1

In Expression 1, C is the bilirubin concentration, $I(\lambda_1)$ is the intensity of reflected light of blue light, $I_0(\lambda_1)$ is the intensity of blue light incident on the skin of the subject, $I(\lambda_2)$ is the intensity of reflected light of green light, $I_0(\lambda_2)$ is the intensity of the green light incident on the skin of the subject, and D and R are specific constants determined for each subject.

Figure 7:
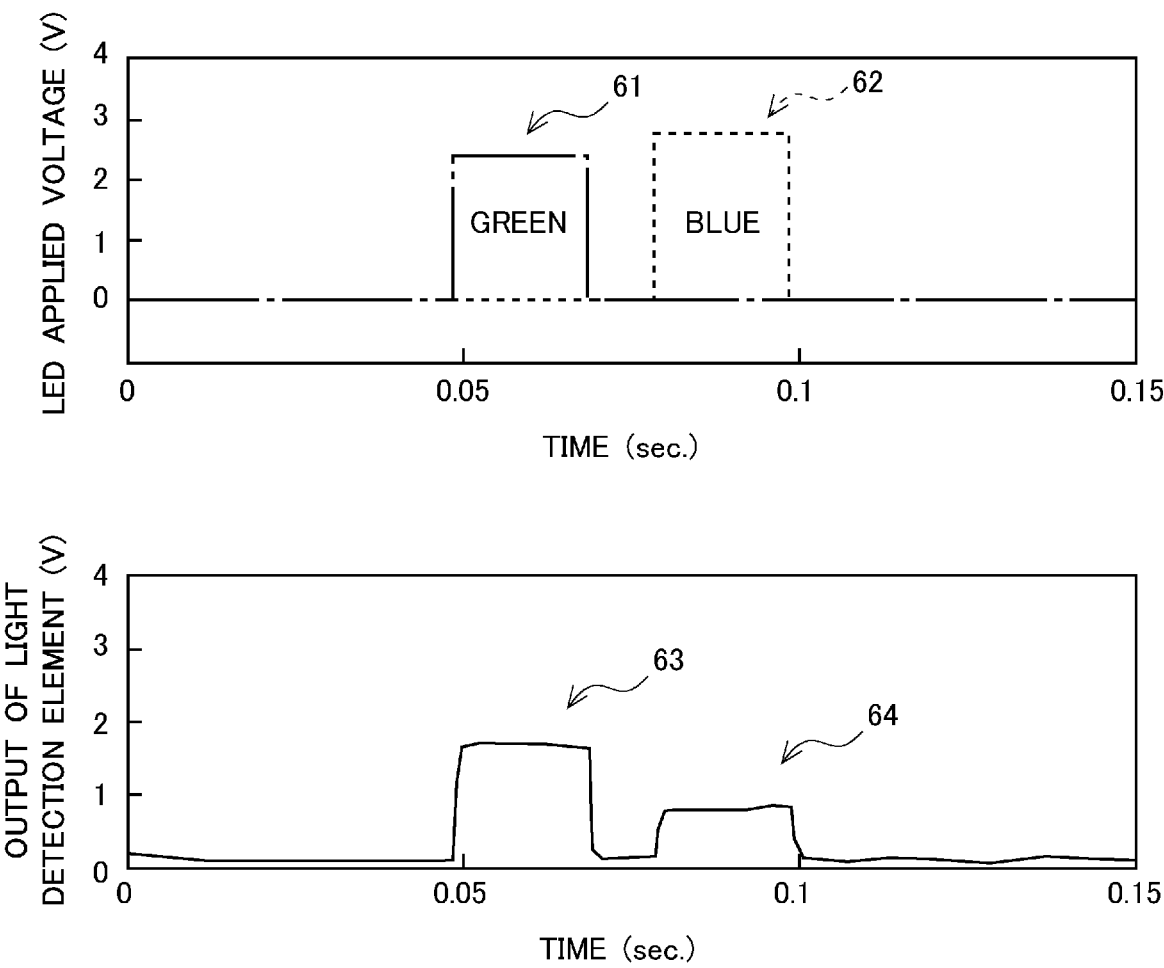
FIG. 7 is a diagram for illustrating a bilirubin concentration measurement timing.

When the bilirubin concentration is measured, the control circuit 11 causes the light emitting elements 12 and 13 to emit light at timings shown in FIG. 7, for example. That is, the control circuit 11 applies a rectangular pulse voltage 61 to the light emitting element 13 to cause the light emitting element 13 to emit green light. After the green light from the light emitting element 13 is incident on the skin of the subject, the green light incident on the skin is reflected by the skin of the subject. The reflected light reflected this time is converted into an electric signal (voltage signal) 63 by the light detection element 14.

Subsequently, the control circuit 11 applies a rectangular pulse voltage 62 to the light emitting element 12 to cause the light emitting element 12 to emit blue light. After the blue light from the light emitting element 12 is incident on the skin of the subject, the blue light incident on the skin is reflected by the skin of the subject. The reflected light reflected this time is converted into an electric signal (voltage signal) 64 by the light detection element 14.

In the above example, the light emitting element 12 (blue light) emits light after the light emitting element 13 (green light). The order thereof may be inverted. The blue light has a higher absorptance of light in bilirubin than the green light. Accordingly, as shown in the lower diagram of FIG. 7, the electric signal 64 corresponding to the blue light has a lower value of the electric signal 63 corresponding to the green light.

The electric signals 63 and 64 detected by the light detection element 14 are wirelessly transmitted as information about the intensities of the reflected light, from the sensor device 10 to the terminal device 20. The computing unit 22 of the terminal device 20 calculates the bilirubin concentration, using the information about the intensities of the reflected light obtained from the sensor device 10, and Expression 1 described above.

Specifically, the bilirubin concentration C can be obtained by substituting, in Expression 1, the intensity $I(\lambda_1)$ of the reflected light of blue light and the intensity $I(\lambda_2)$ of the reflected light of green light, which are the information about the intensities of the reflected light. Here, $I_0(\lambda_1)$ is the intensity of blue light incident on the skin of the subject, and is a value according to the drive voltage supplied from the control circuit 11 to the light emitting element 12, and the property of the light emitting element 12. Accordingly, this value is a known value. Likewise, $I_0(\lambda_2)$ is the intensity of green light incident on the skin of the subject, and is a value according to the drive voltage supplied from the control circuit 11 to the light emitting element 13, and the property of the light emitting element 13. Accordingly, this value is a known value. D and R are specific constants determined for each subject. Consequently, the bilirubin concentration C can be obtained by substituting, in Expression 1, the intensity $I(\lambda_1)$ of the reflected light of blue light and the intensity $I(\lambda_2)$ of the reflected light of green light, which are the information about the intensities of the reflected light. Note that in Expression 1, "$I(\lambda_1)/I_0(\lambda_1)$" corresponds to the transmittance of blue light, and "$I(\lambda_2)/I_0(\lambda_2)$" corresponds to the transmittance of green light.

As described above, D and R are specific constants determined for each subject. D is the constant corresponding to the length of a path along which light propagates in the subject. R is the constant corresponding to attenuation of light in the subject.

In this embodiment, the computing unit 22 preliminarily measures the bilirubin concentration of each subject to be tested, using other means and/or the bilirubin concentration measurement system 1, and predetermines the constant D and the constant R in the Expression 1 for each subject to be tested, using the bilirubin concentration measured using the other means and/or the bilirubin concentration measurement system 1. Hereinafter, a method of determining the constants D and R is described.

First, the bilirubin concentration is preliminarily measured for each subject to be tested, using other means (a blood test etc.). Each of the light emitting elements 12 and 13 of the sensor device 10 is caused to emit light multiple times to obtain multiple data on combinations between the intensities $I(\lambda_1)$ of the reflected light of blue light and the intensities $I(\lambda_2)$ of the reflected light of green light.

The bilirubin concentration C preliminarily obtained using the other means, and the multiple values of intensities $I(\lambda_1)$ and $I(\lambda_2)$, are substituted in Expression 1, thereby creating simultaneous equations. The unknown constants are the two constants, which are D and R. Accordingly, in principle, the constants D and R can be obtained by solving the two simultaneous equations. For example, multiple constants D and R are obtained, and the obtained constants D and R are statistically processed (for example, mean values are obtained), thereby allowing the accuracies of the constants D and R to be improved. Through use of such a method, the constant D and the constant R can be predetermined for each subject to be tested.

In a case where measurement of variation from an initial value is sufficient for measurement of the bilirubin concentration of a subject (i.e., a case where the relative value of the bilirubin concentration is calculated but the absolute value is not required to be measured), preliminary measurement of the bilirubin concentration using other means (blood test etc.) is unnecessary. That is, in the case where the variation in bilirubin concentration (relative value) is obtained, the constants D and R are temporarily determined. For example, the values of the constants D and R may be determined using previously used data on the constants D and R. The bilirubin concentration measurement system 1 is then used to obtain the intensity $I(\lambda_1)$ of the reflected light of blue light, and the intensity $I(\lambda_2)$ of the reflected light of green light are obtained, and the values of $I(\lambda_1)$ and $I(\lambda_2)$ are substituted in Expression 1, which can obtain the variation in bilirubin concentration (relative value).

As described above, in the case where the constants D and R are predetermined, the absolute value of the bilirubin concentration is subsequently obtained using other means (blood test etc.), thereby allowing the preliminarily obtained relative value of the bilirubin concentration to be converted into the absolute value.

Figure 8:
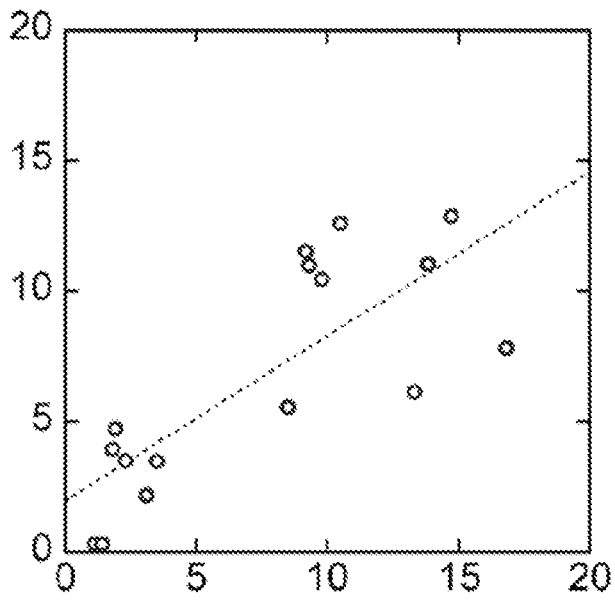
FIG. 8 is a graph showing the relationship between values measured using a commercially available bilirubin concentration measurement apparatus (abscissa axis) and values measured using a bilirubin concentration measurement system according to the present invention (ordinate axis).

FIG. 8 is a graph showing the relationship between values measured using a commercially available bilirubin concentration measurement apparatus (apparatus A: R=0.77) (abscissa axis) and values measured using a bilirubin concentration measurement system according to the present invention (apparatus B) (ordinate axis). In FIG. 8, bilirubin concentrations are obtained for each subject through the two apparatuses, which are the apparatus A and the apparatus B, and these values are plotted. The plotted values correspond respective subjects. When the bilirubin concentration is measured using the bilirubin concentration measurement system according to the present invention, blue light and green light are alternatively emitted every 40 ms, as shown in FIG. 7.

As shown in FIG. 8, there is a relationship between the values measured using the bilirubin concentration measurement system according to this embodiment (ordinate axis) and the values measured using the commercially available bilirubin concentration measurement apparatus (abscissa axis). That is, the bilirubin concentration measurement system according to this embodiment has a measurement accuracy equivalent to that of the commercially available bilirubin concentration measurement apparatus.

The bilirubin concentration measurement system 1 according to this embodiment includes: the sensor device 10 attachable to a subject; and the terminal device 20 capable of wirelessly communicating with the sensor device 10. The sensor device 10 has the configuration that includes the light emitting elements 12 and 13 and the light detection elements 14. The bilirubin concentration is calculated by the terminal device 20. Consequently, the configuration of the sensor device 10 can be simplified, which can reduce the size of the sensor device 10.

The sensor device 10 according to this embodiment can be attached to the subject in a state of being in close contact, and continuously monitor the bilirubin concentration of the subject accordingly. That is, the light emitting elements 12 and 13 can be caused to emit light alternately, and reflected light at this time is detected by the light detection element 14, which can continuously monitor the bilirubin concentration of the subject.

Consequently, the invention according to this embodiment can provide the bilirubin concentration measurement system that is small in size and capable of continuously monitoring the bilirubin concentration.

Figure 9:
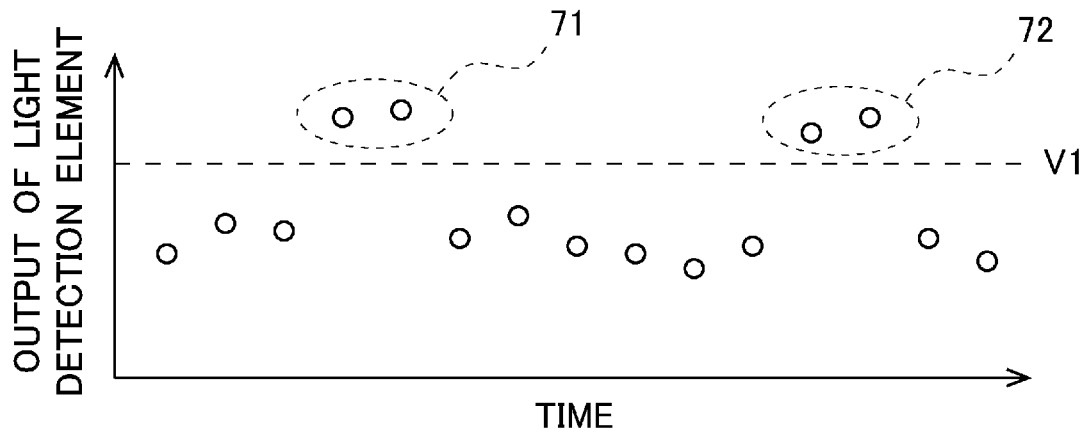
FIG. 9 is a diagram for illustrating an example of temporal change in output of a light detection element.

FIG. 9 is a diagram for illustrating an example of temporal change in output of the light detection element 14, and shows temporal change when reflected light having a predetermined color (blue or green) is detected by the light detection element 14. As shown in FIG. 9, the light detection element 14 continuously detects the reflected light. However, the outputs of the light detection element 14 sometimes include data 71 and 72 having higher voltages than a predetermined value V1 (i.e., data having high light intensities). It is assumed that this is because the light detection element 14 is temporarily apart from the subject owing to, for example, movement of the subject, and an abnormality temporarily occurs in reflected light detection.

In such a case, the computing unit 22 may exclude the data 71 and 72 temporarily having a higher voltage than the predetermined value V1 (i.e., data having high light intensities), and calculate the bilirubin concentration. The computing unit 22 can accurately calculate the bilirubin concentration by excluding such abnormal data 71 and 72.

Figure 10:
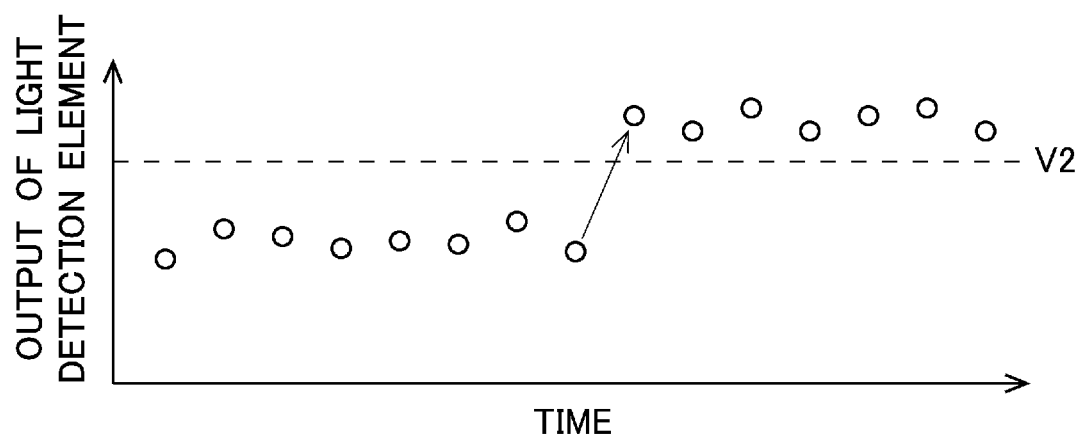
FIG. 10 is a diagram for illustrating an example of temporal change in output of the light detection element.

FIG. 10 is a diagram for illustrating an example of temporal change in output of the light detection element 14, and shows temporal change when reflected light having a predetermined color (blue or green) is detected by the light detection element 14. As shown in FIG. 10, while the light detection element 14 continuously detects reflected light, the output of the light detection element 14 becomes higher than a predetermined value V2 at a certain timing (see an arrow in the graph of FIG. 10) and the state is continued in some cases. It is assumed that this is because the sensor device 10 (light detection element 14) is apart from the subject owing to, for example, movement of the subject, and an abnormality occurs in reflected light detection.

In such a case, the computing unit 22 can determine that the sensor device 10 is not correctly attached on the subject. For example, when the computing unit 22 determines that the state of the sensor device 10 is abnormal, a warning message indicating that the state of the sensor device 10 is abnormal may be displayed on the display unit 23. A warning sound may be output from the speaker included in the terminal device 20.

As described above, the bilirubin concentration measurement system 1 according to this embodiment can be preferably used for bilirubin measurement for newborns (babies and infants). However, the close contact between the sensor device 10 and the skin of a newborn becomes insufficient by movement of the newborn, and light from the light emitting elements 12 and 13 is reflected by the surface of the skin of the newborn in some cases. In such cases, the reflected light serves as a disturbance. Accordingly, the accuracy of the measured value of the bilirubin concentration sometimes decreases.

The bilirubin concentration measurement system 1 according to this embodiment may apply predetermined statistical processing to the output data of the light detection elements 14 in order to reduce the adverse effects of such a disturbance.

That is, the light emitting element 12 (blue light) is caused to emit light multiple times, and reflected light at the times is detected multiple times by the light detection element 14. The computing unit 22 applies the predetermined statistical processing to data corresponding to the intensities of reflected light (reflected light of blue light) detected multiple times. Among statistically processed data corresponding to the intensity of the reflected light, data in a predetermined range are selectively used to calculate the bilirubin concentration. Likewise, the light emitting element 13 (green light) is caused to emit light multiple times, and reflected light at the times is detected multiple times by the light detection element 14. The computing unit 22 applies the predetermined statistical processing to data corresponding to the intensities of reflected light (reflected light of green light) detected multiple times. Among statistically processed data corresponding to the intensity of the reflected light, data in a predetermined range are selectively used to calculate the bilirubin concentration.

Specifically, the computing unit 22 classifies the data corresponding to the intensities of the reflected light detected multiple times, into multiple classes corresponding to the intensities of the reflected light. The bilirubin concentration is then calculated, selectively using data having cumulative relative frequencies in a predetermined range, among the classified data corresponding to the intensities of the reflected light. At this time, the computing unit 22 may calculate the bilirubin concentration using the mean value of the selected data. The computing unit 22 applies such processes to each of the reflected light of the light emitting element 12 (blue light) and the reflected light of the light emitting element 13 (green light).

Figure 11:
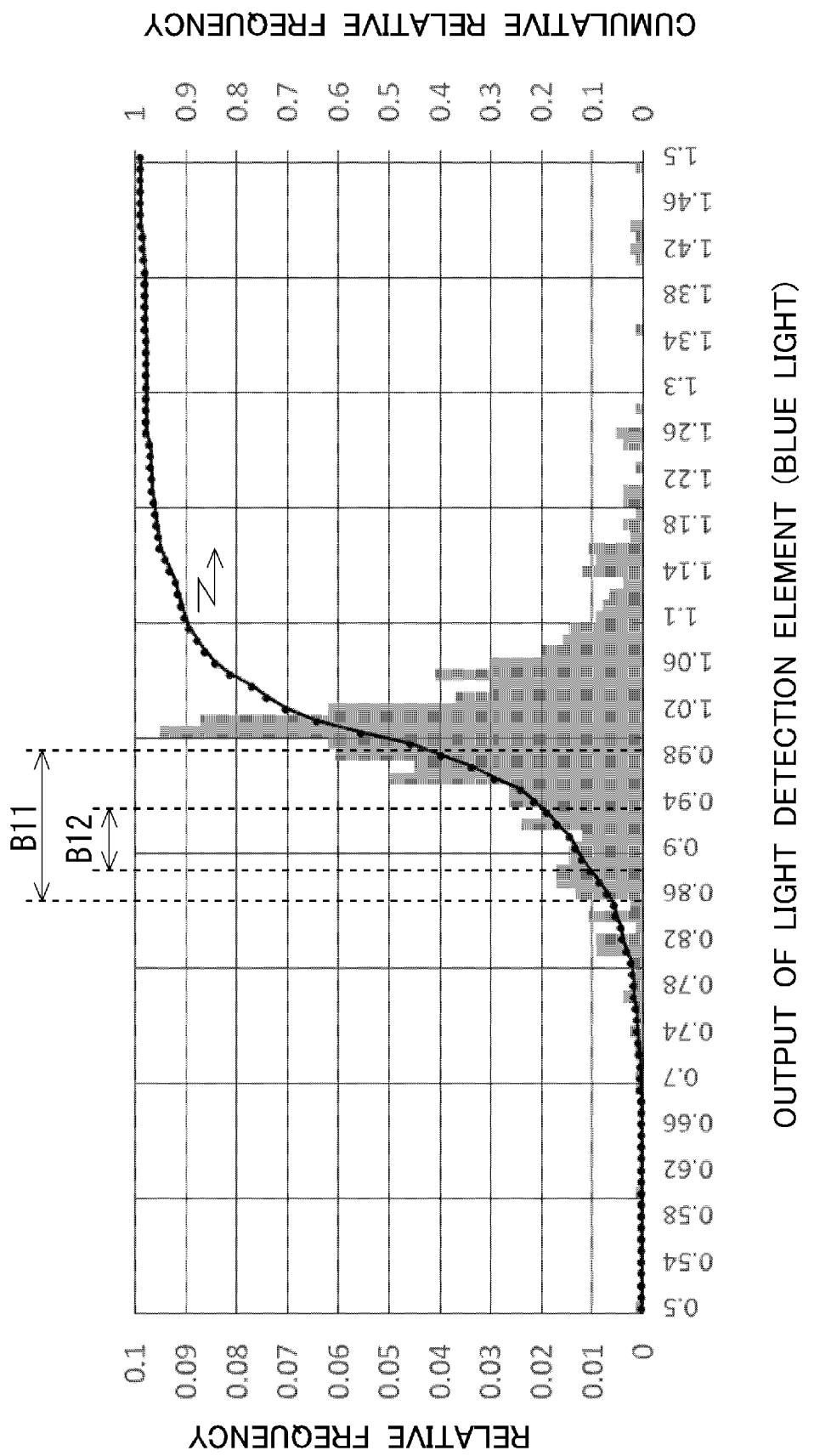
FIG. 11 is a graph showing an example where statistical processing is applied to the output of the light detection element (blue light).
Figure 12:
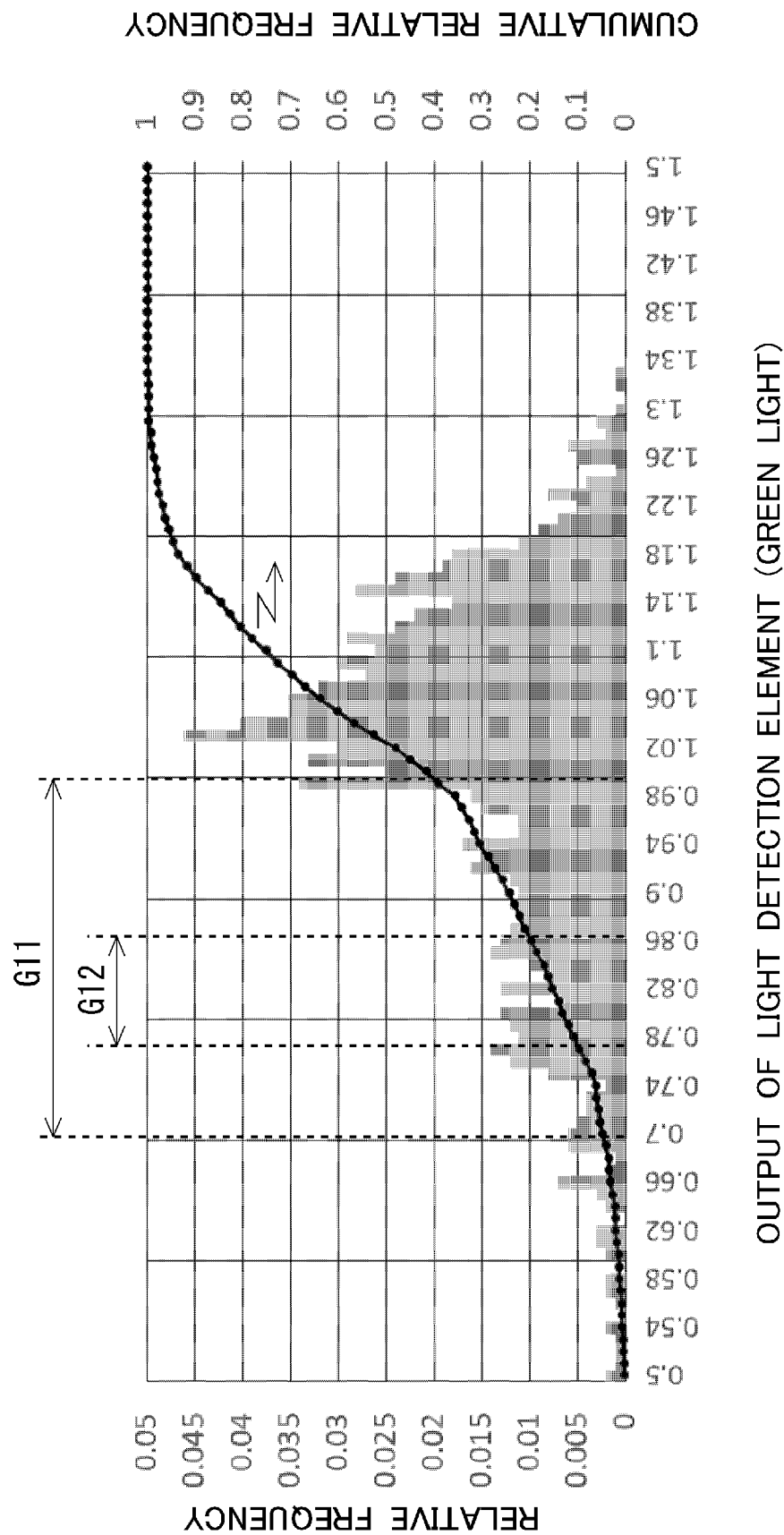
FIG. 12 is a graph showing an example where statistical processing is applied to the output of the light detection element (green light).

Hereinafter, a specific example of such statistical processing is described with reference to FIGS. 11 and 12. FIG. 11 is a graph showing an example where the statistical processing is applied to the output of the light detection element (blue light). FIG. 12 is a graph showing an example where the statistical processing is applied to the output of the light detection element (green light). FIGS. 11 and 12 indicate histograms of the outputs of the light detection element 14.

In FIGS. 11 and 12, the abscissa axes indicate the outputs of the light detection element 14, and correspond to the intensities of the reflected light. Each abscissa axis is classified into multiple classes corresponding to the intensities of the reflected light. Data corresponding to the reflected light detected by the light detection element 14 (e.g., electric signal values of the light detection element 14) are classified into multiple classes. Each ordinate axis (left side) indicates the relative frequency. That is, the ordinate axis (left side) indicates the value (frequency) obtained by dividing the number of data classified into the individual classes by the number of total measured data (the number of total measurement times). Curves in the graphs of FIGS. 11 and 12 indicate the integrated values of the relative frequencies, that is, the cumulative relative frequencies (the ordinate axis on the left side).

The graph shown in FIG. 11 shows results of continuous measurement for about 30 seconds, with the light emitting element 12 (blue light) being caused to emit light for about three seconds, in order to survey the overview of the output (electric signal value) of the light detection element 14. FIG. 11 collectively shows measured results of 75 babies and infants, and the number of total measurement times is 757. Likewise, the graph shown in FIG. 12 indicates results of continuous measurement for about 10 seconds, with the light emitting element 13 (green light) being caused to emit light for about 0.2 seconds. FIG. 12 collectively shows measured results of 14 babies and infants, and the number of total measurement times is 996. Note that during measurement, the light emitting element 12 (blue light) and the light emitting element 13 (green light) are alternately caused to emit light, and the individual reflected light is measured.

In FIGS. 11 and 12, each part where the output (electric signal value) of the light detection element 14 is high are considered as reflected light that is light from the light emitting elements 12 and 13 reflected by the surface of the skin, that is, a disturbance. Accordingly, in this embodiment, among the outputs (electric signal values) of the light detection element 14, data having low values (i.e., data of the reflected light having reached below the skin and been reflected) are selectively used, which can improve the accuracy of the measured value of the bilirubin concentration.

Here, the data having low values are data in a range having the cumulative relative frequencies from 0.05 to 0.4 shown in FIGS. 11 and 12. Specifically, the data are the outputs (electric signal values) of the light detection element 14 in a range B11 shown in FIG. 11. The outputs (electric signal values) of the light detection element 14 in a range G11 shown in FIG. 12.

For example, the mean value of the outputs (electric signal values) of the light detection element 14 in the range B11 indicated in FIG. 11 may be obtained, and the mean value may be used as information about the intensities of the reflected light of blue light. That is, the mean value may be used as the value of the intensity $I(\lambda_1)$ of the reflected light of blue light in Expression 1. Likewise, the mean value of the outputs (electric signal values) of the light detection element 14 in the range G11 indicated in FIG. 12 may be obtained, and the mean value may be used as information about the intensities of the reflected light of green light. That is, the mean value may be used as the value of the intensity $I(\lambda_2)$ of the reflected light of green light in Expression 1. These values may be used to obtain the constant D and the constant R in Expression 1. The bilirubin concentration can be accurately obtained using such a method.

Note that in this embodiment, data in any range may be selected to be used only if the data are included in the range B11 shown in FIG. 11. Likewise, data in any range may be selected to be used only if the data are included in the range G11 shown in FIG. 12.

In particular, in this embodiment, it is preferable to use data having the cumulative relative frequencies ranging from 0.1 to 0.2 shown in FIGS. 11 and 12. Specifically, it is preferable to use the outputs (electric signal values) of the light detection element 14 in a range B12 shown in FIG. 11. Furthermore, it is preferable to use the outputs (electric signal values) of the light detection element 14 in a range G12 shown in FIG. 12.

In a case of obtaining the bilirubin concentration using values in the range B12 shown in FIG. 11 and values in the range G12 shown in FIG. 12, the correlation with the bilirubin concentration measured using the commercially available bilirubin concentration measurement apparatus (apparatus A: R=0.77) was specifically favorable.

Note that FIGS. 11 and 12 show data on multiple babies and infants in order to survey the overview of the output (electric signal value) of the light detection element 14. However, in actual measurement, for example, by repeating for about 10 seconds one time of emission and detection of light every period ranging from 0.05 to 0.5 seconds for each of the babies and infants, 100 measured data on the reflected light of blue light, and 100 measured data on the reflected light of green light can be obtained at the maximum. The bilirubin concentration can be accurately obtained by applying such a method to the data obtained as described above.

Figure 13:
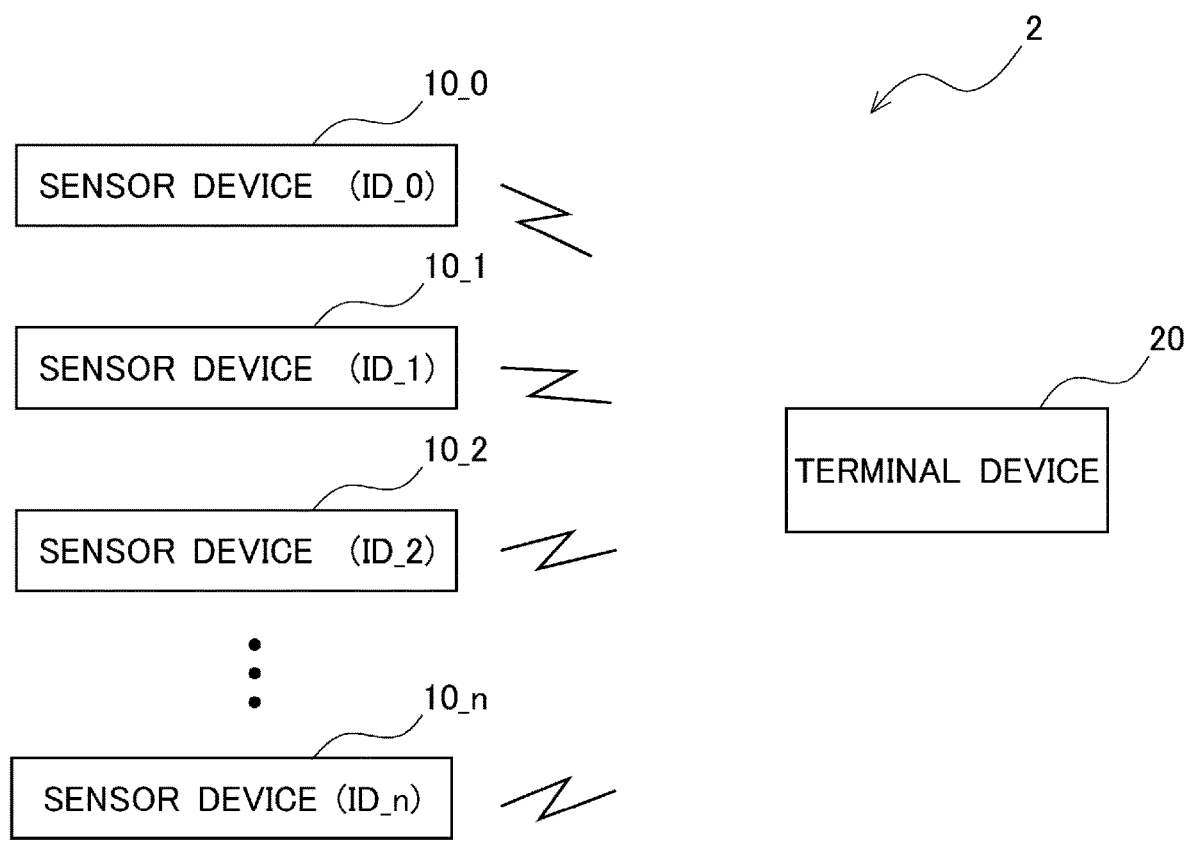
FIG. 13 is a block diagram for illustrating a system configuration example of the bilirubin concentration measurement system according to the embodiment.

FIG. 13 is a block diagram for illustrating a system configuration example of a bilirubin concentration measurement system according to this embodiment. The bilirubin concentration measurement system 2 shown in FIG. 13 includes multiple sensor devices 10_0 to 10_n (n is an integer of one or more), and a terminal device 20 capable of communicating with these sensor devices 10_0 to 10_n. For example, the bilirubin concentration measurement system 2 shown in FIG. 13 can be used as a system that collectively manages the bilirubin concentrations of multiple newborns in a hospital or the like. That is, the sensor devices 10_0 to 10_n are attached to the respective newborns, and information about the intensities of the reflected light is wirelessly transmitted from each of the sensor devices 10_0 to 10_n to the terminal device 20. Accordingly, the terminal device 20 can collectively manage the bilirubin concentrations of the individual newborns.

At this time, the communication units 16 of the sensor devices 10_0 to 10_n respectively add pieces of ID information unique to the sensor devices 10_0 to 10_n, and wirelessly transmit the information about the intensities of the reflected light to the terminal device 20. Accordingly, the terminal device 20 can identify the transmitter of the information about the intensities of the reflected light, using the added ID information.

As described above, the bilirubin concentration measurement system 2 according to this embodiment wirelessly transmits the data from the sensor devices 10_0 to 10_n to the terminal device 20. Accordingly, wiring for connecting the sensor devices with the terminal device can be omitted, which can improve the work environment for nurses and the like in the hospital or the like.

As for the bilirubin concentration measurement system according to this embodiment described above, the case of measuring the bilirubin concentration of the subject using the sensor device 10 has been described. However, this embodiment may have a configuration that detects information other than that on the bilirubin concentration using the sensor device 10. For example, multiple vital signs, such as the pulse rate, respiration rate, heart rate, body temperature, brain waves (EEG: electroencephalogram), and blood oxygen saturation level, may be measured over time.

Figure 14:
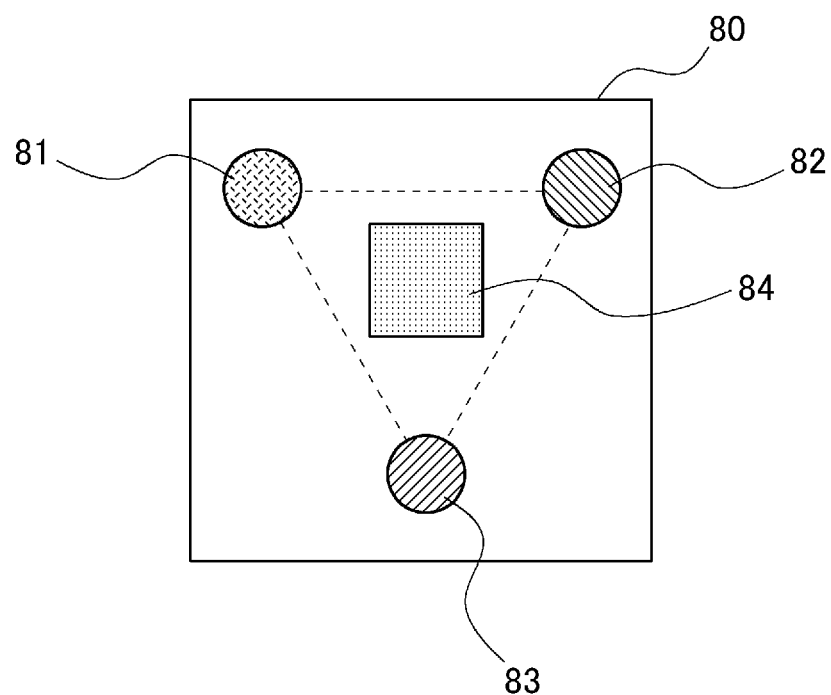
FIG. 14 is a diagram for illustrating another configuration example of the sensor device according to the embodiment.

FIG. 14 is a diagram for illustrating another configuration example of a sensor device included in a bilirubin concentration measurement system according to this embodiment. In the sensor device shown in FIG. 14, three light emitting elements 81 to 83, and a light detection element 84 are implemented on a substrate 80. In the configuration shown in FIG. 14, the light detection element 84 is arranged at the center position of the three light emitting elements 81 to 83. The three light emitting elements 81 to 83 are elements that emit red light, green light, and blue light, respectively. In the sensor device shown in FIG. 14, when the bilirubin concentration is measured, the light emitting element 82 (green light) and the light emitting element 83 (blue light) are used for measuring the bilirubin concentration. For measuring the blood oxygen saturation level, the light emitting element 81 (red light) and the light emitting element 82 (green light) are used. As described above, the sensor device is provided with the three light emitting elements 81 to 83, which can measure the bilirubin concentration and measure the blood oxygen saturation level. By further implementing a thermistor in the sensor device, the body temperature of a subject can be measured. Such information is wirelessly transmitted to the terminal device 20. Accordingly, multiple vital signs of the subject can be monitored over time in the terminal device 20.

The present invention has thus been described based on the aforementioned embodiments. However, the present invention is not limited only to the configuration of the aforementioned embodiment. It is a matter of course that the present invention encompasses various changes, modifications and combinations that those skilled in the art can make within the scope of the invention defined by each claim of the claims in the present application.

This application claims the priority based on Japanese Patent Application No. 2018-239555, filed Dec. 21, 2018, disclosure of which is herein incorporated by reference in its entirety.

REFERENCE SIGNS LIST 1, 2 Bilirubin concentration measurement system
10 Sensor device
11 Control circuit
12, 13 Light emitting element
14 Light detection element
15 Amplifier
16 Communication unit
20 Terminal device
21 Communication unit
22 Computing unit
23 Display unit
30 Substrate
41 Exterior resin
42 Substrate
45 Battery
47 Subject
48 Blood vessel
51 Bilirubin solution
52 Blue light emitting element
53 Green light emitting element
54 Light detection element
55 Detector
80 Substrate
81, 82, 83 Light emitting element
84 Light detection element

The invention claimed is:

1. A bilirubin concentration measurement system, comprising: a sensor device attachable to a subject; and a terminal device capable of wirelessly communicating with the sensor device, wherein
the sensor device comprises:
a first light emitting diode configured to emit light in a first wavelength band at a first timing on skin of the subject to produce first reflected light;
a second light emitting diode configured to emit light in a second wavelength band at a second timing on the skin of the subject to produce second reflected light;
a photodiode configured to detect the first reflected light that is the light in the first wavelength band having been incident on the skin of the subject and been reflected at the first timing, and detect the second reflected light that is the light in the second wavelength band having been incident on the skin of the subject and been reflected at the second timing; and
a first communication unit comprising a transmitter configured to wirelessly transmit information about intensities of the first and second reflected light detected by the photodiode, and
the terminal device comprises:
a second communication unit comprising a receiver configured to receive the information about the intensities of the first and second reflected light transmitted from the first communication unit; and
a computing unit configured to calculate a bilirubin concentration,
wherein:
the photodiode is configured to detect, multiple times, each of the first and second reflected light at the first and second timings, and the computing unit is configured to:
- apply predetermined statistical processing to data corresponding to the intensities of the first and second reflected light detected multiple times, and
- classify the data corresponding to the intensities of the first and second reflected light detected multiple times into a plurality of classes corresponding to the intensities of the reflected light,
- wherein calculating the bilirubin concentration comprises selectively using data having cumulative relative frequencies in a predetermined range among the classified data corresponding to the intensities of the first and second reflected light, wherein the predetermined range is 0.05 to 0.4, wherein:
- the sensor device further comprises an exterior resin that encloses a substrate on which the first and second light emitting diodes and the photodiode are implemented,
- light emitting surfaces of the first and second light emitting diodes and a light receiving surface of the photodiode are exposed from a surface of the exterior resin configured to face the subject, and
- the surface of the exterior resin facing the subject has a shape corresponding to a shape of a part of the subject to which the sensor device is attached.

2. The bilirubin concentration measurement system according to claim 1, wherein
calculating the bilirubin concentration comprises using a following Expression 1, $$C = D\left[-\log_{10}\frac{I(\lambda_1)}{I_0(\lambda_1)} + 1.95\log_{10}\frac{I(\lambda_2)}{I_0(\lambda_2)} + R\right] \quad \text{Expression 1}$$

wherein, in the Expression 1, C is the bilirubin concentration, $I(\lambda_1)$ is the intensity of the first reflected light, $I_0(\lambda_1)$ is an intensity of the light in the first wavelength band incident on the skin of the subject, $I(\lambda_2)$ is the intensity of the second reflected light, $I_0(\lambda_2)$ is an intensity of the light in the second wavelength band incident on the skin of the subject, and D and R are specific constants determined for the subject.

3. The bilirubin concentration measurement system according to claim 2, wherein the computing unit is configured to preliminarily measure the bilirubin concentration of the subject to be tested using other means, and predetermine the constant D and the constant R in the Expression 1 for the subject using the bilirubin concentration measured using the other means.

4. The bilirubin concentration measurement system according to claim 1, wherein
the computing unit is configured to exclude data having a higher intensity than a predetermined value among the intensities of the first and second reflected light detected multiple times.

5. The bilirubin concentration measurement system according to claim 1, wherein when the intensities of the first and second reflected light are higher than a predetermined value, the computing unit is configured to determine that the sensor device is not correctly attached to the subject.

6. The bilirubin concentration measurement system according to claim 1, wherein calculating the bilirubin concentration comprises using mean values of the selected data.

7. The bilirubin concentration measurement system according to claim 1, wherein calculating the bilirubin concentration comprises selectively using data having the cumulative relative frequencies ranging from 0.1 to 0.2.

8. The bilirubin concentration measurement system according to claim 1, wherein:
- the bilirubin concentration measurement system further comprises a plurality of the sensor devices;
- the terminal device is capable of communicating with the sensor devices;
- the first communication unit of each of the sensor devices is configured to add ID information unique to the corresponding sensor device to the information about the intensities of the first and second reflected light, and wirelessly transmit the information; and
- the terminal device is configured to identify a transmitter of the information about the intensities of the first and second reflected light using the ID information.

* * * * *